United States Patent
Starta et al.

(10) Patent No.: US 7,132,659 B2
(45) Date of Patent: Nov. 7, 2006

(54) SENSOR HAVING A COMMUNICATION DEVICE, SENSOR COMMUNICATION SYSTEM AND METHOD OF COMMUNICATING INFORMATION FROM A SENSOR

(75) Inventors: Christopher D. Starta, Pittsburgh, PA (US); Leonard J. Blatnica, Delmont, PA (US); Mark Shomali, Cranberry Township, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 241 days.

(21) Appl. No.: 10/785,635

(22) Filed: Feb. 24, 2004

(65) Prior Publication Data

US 2005/0127297 A1 Jun. 16, 2005

Related U.S. Application Data

(60) Provisional application No. 60/529,351, filed on Dec. 12, 2003.

(51) Int. Cl.
G01J 5/02 (2006.01)
(52) U.S. Cl. .................................... 250/341.5
(58) Field of Classification Search ............. 250/341.5
See application file for complete search history.

(56) References Cited

U.S. PATENT DOCUMENTS 5,025,653 A * 6/1991 Schuldt ...................... 73/23.2
5,321,492 A * 6/1994 Detwiler et al. .............. 356/73
5,923,035 A 7/1999 Winkler et al.
6,538,728 B1 3/2003 Stolle et al.

FOREIGN PATENT DOCUMENTS

EP 1 281 977 A1 2/2003
WO WO 03/014714 A1 2/2003

* cited by examiner

*Primary Examiner*—Constantine Hannaher
(74) *Attorney, Agent, or Firm*—James G. Uber; Henry E. Bartony, Jr.

(57) ABSTRACT

A method of communicating information from a sensor includes the step of modulating the emission of energy from an energy source in a manner that corresponds to information to be transmitted from the sensor through a transmissive section in the sensor housing. Energy from the energy source, which is within the housing of the sensor, also interacts with an analyte in a detectable manner. A sensor for detecting the presence of an analyte in an environment being tested includes a housing, an energy source within the housing, at least one detector within the housing adapted to detect interaction between energy emitted by the energy source and the analyte, a transmissive section in the housing through which energy emitted from the energy source can be transmitted; and a controller within the housing in operative connection with the energy source to modulate emission of energy from the energy source in a manner to communicate information through the transmissive section.

19 Claims, 6 Drawing Sheets

SENSOR HAVING A COMMUNICATION DEVICE, SENSOR COMMUNICATION SYSTEM AND METHOD OF COMMUNICATING INFORMATION FROM A SENSOR

CROSS-REFRENCE TO RELATED APPLICATION

This application claims the benefit of U.S. Provisional Patent Application Ser. No. 60/529,351. filed Dec. 12, 2003 the disclosure of which is incorporated herein by reference.

FIELD OF THE INVENTION

The present invention relates generally to a sensor having a communication device, to a sensor communicating system and to a method of communicating information from a sensor, and particularly to devices, systems and methods for communicating calibration information from a gas sensor using a detection energy in the light spectrum.

BACKGROUND OF THE INVENTION

Infrared gas sensors use an infrared energy source to detect the presence of an analyte in an environment being tested. In general, the analyte absorbs infrared energy of a certain wavelength and this absorption can be quantified to determine the concentration of the analyte in the test environment. Several embodiments, of infrared fluid sensors or analyzers are discussed, for example, in U.S. Pat. Nos. 4,355,234, 4,598,201 and 4,902,896, assigned to the assignee of the present invention, the disclosures of which are incorporated herein by reference.

An example of a commercially available infrared gas sensor is the ULTIMA® XIR Gas Monitor, available from Mine Safety Appliances Company of Pittsburgh, Pa. The operation of that sensor is discussed in detail in the ULTIMA X Series Gas Monitors Instruction Manual available from Mine Safety Appliances Company, Instrument Division, the disclosure of which is incorporated herein by reference.

In general, the ULTIMA XIR Gas Monitor uses an electronically modulated source of infrared energy and two detectors that convert the infrared energy into electrical signals. The source of infrared energy emits light energy over a broad spectrum of wavelengths, including visible light. The light passes through two different wavelength filters. Each detector is sensitive to a different range of wavelengths in the infrared portion of the light spectrum. The source emission is directed through a window in the main enclosure into an open volume. A mirror at the end of this volume, protected by a second window, directs the energy back through the window in the main enclosure and onto the detectors. During operation of the sensor, the open volume is surrounded by a cap through which environmental gas can pass, but which protects the volume from exposure to wind and other environmental elements that might cause erroneous or erratic readings. The presence of an analyte gas in the open volume reduces the intensity of the source emission measured by the analytical detector but not the intensity of the source emission measured by the reference detector. In that regard, the reference detector measures infrared intensity at a wavelength outside of the analyte absorption range. A microprocessor monitors the ratio of the two signals and, in the case of a combustible gas, for example, correlates the ratio into a % Lower Explosion Limit (LEL) combustible reading.

Typically, infrared gas sensors are initially calibrated by the manufacturer. However, periodic recalibration of the sensor is often desirable. Under current practice, calibration techniques for infrared sensors require the use of an intelligent external calibration device. Such calibration devices typically communicate with a main monitor unit to which the infrared sensor is attached at the sensing location. The main monitor unit typically includes a user feedback display and appropriate communications circuitry (to communicate with a control center remote from the sensor as well as with an external calibration device) enclosed within a housing that is specifically designed for use in a hazardous location (for example, the housing and display unit window can form an explosion-proof enclosure in the case of a monitor for combustible hydrocarbons). For example, an ULTIMA X Calibrator or an ULTIMA X Controller is available for use with the ULTIMA XIR Gas Monitor. Those units are hand-held, battery-powered units, that allow one person, non-intrusive calibration of the ULTIMA XIR Gas Monitor without opening the monitor or sensor housings. Use of the ULTIMA X Calibrator and Controller is described in the ULTIMA/ULTIMA X Series Controller and Calibrator Instruction Manual, available from Mine Safety Appliances Company, Instrument Division, the disclosure of which is incorporated herein by reference.

During calibration of a gas sensor, one or more sample or calibration gases having a known concentration of analyte gas (or a simulant gas) are preferably applied directly to the sensor. Typically a "zero" gas, having no analyte therein, is applied to the sensor during calibration. A "span" gas, having a known, non-zero analyte (or simulant) concentration, can also be applied during calibration. Often, the concentration of analyte (or simulant) in the span gas is approximately at the midrange of the overall concentration range of the sensor. In many cases, it is necessary to perform only a zero gas procedure in periodically calibrating an infrared gas sensor, as restoring the sensor's zero performance is typically sufficient to restore the sensor's span performance.

An intelligent calibrator such as the ULTIMA X Calibrator or the ULTIMA X Controller can communicate with the gas monitor/sensor (using, for example, infrared energy or radio frequency energy) to place the sensor in a calibration mode. Various inputs are provided on the calibrator to communicate any number of functions to the gas monitor to initiate, for example, a zero procedure, zero and span procedures, a network address change, a span value change etc. In general, such intelligent calibrators operate very well. However, relatively complicated electronics in both the calibrator and monitor are often required, resulting in substantial expense and operational complexity. Moreover, in the case of infrared sensors for point detection of combustible gas(es) the calibrator must be housed in an explosion-proof housing or be intrinsically safe, adding further expense.

It is thus desirable to develop alternative communication/calibration devices, systems and methods that are relatively inexpensive and easy to operate.

SUMMARY OF THE INVENTION

In one embodiment, the present invention provides a method of communicating information from a sensor. The sensor includes a source of energy within a housing thereof. Energy from the energy source interacts with an analyte in a detectable manner. The sensor further has at least one transmissive section in the housing through which energy can be transmitted. The method includes the step of modulating the emission of energy from the energy source in a manner that corresponds to information to be transmitted from the sensor through the transmissive section. As used herein, the term "modulation" refers to any change in the emission of the energy source so as to transmit information. In that regard, for example, one or more of the frequency, duty cycle, intensity etc. of the energy source can be altered or changed in a manner so as to transmit information.

Preferably, the sensor has at least a sensing mode in which the energy source operates to interact with an analyte that may be present in an environment being tested and a communication mode in which the energy source operates to communicate information through the transmissive section. The method preferably further includes the step of initiating the communication mode by placing an activator in operative connection with the sensor.

In one embodiment the energy source is an infrared energy source and the transmissive section is a window in the housing of the sensor. The infrared energy source can, for example, emit energy over a range of the light spectrum including in the infrared wavelength(s) used for detection and reference functions. The emission range of the infrared energy source can, for example, include energy in the visible range of the spectrum in the communication mode. In this embodiment, it is possible to transmit information directly to a human observer through modulation of the energy source. Alternatively a detector exterior to the housing of the sensor and adapted to sense energy emitted from the energy source in the communication mode can be used.

The housing can, for example, be an explosion-proof housing (for use, for example, in the sensing of combustible gas(es). In the case of an explosion-proof housing, the activator preferably initiates the communication mode in a wireless manner.

Wireless activation of the communication mode can, for example, occur by placing at least one magnet in operative connection with the housing so as to be in operative connection with a switch within the housing of the sensor. In the case of magnetic activation, preferably at least two magnets are placed in operative connection with the housing at two distinct locations, so that each of the magnets is placed in operative connection with a separate switch within the housing of the sensor. Requiring the activation of two switches at different physical locations within the housing reduces the risk of a stray magnetic field placing the sensor in the communication mode.

In one embodiment, the magnets are seated in a cap member that is placed in operative connection with the housing of the sensor. The cap member preferably further includes a detector (as discussed above) that is suitable to detect energy transmitted by the infrared energy source and a display in communicative connection with the detector to display information communicated via modulation of the infrared energy source.

In one embodiment, placing the cap member in operative connection with the housing of the sensor causes the sensor to enter a calibration mode in which information related to calibration of the sensor is transmitted via modulation of the infrared energy source.

The infrared energy source can, for example, be modulated in a manner to indicate that the calibration mode has been initiated. The infrared energy can also be modulated in a manner to detect the analyte during a calibration. After application of a test gas of known analyte (or simulant) concentration (preferably, for a period of time sufficient to reach a generally steady state signal), the infrared energy source is subsequently modulated in a manner to indicate whether the calibration passed or failed. The calibration or test gas applied to the sensor during calibration can, for example, be a zero calibration test gas. Likewise, a span gas can be applied.

The energy source can, for example, emit energy in the light spectrum to interact with the analyte and to transmit information from the sensor through the transmissive section. The energy that interacts with the analyte need not be of the same wavelength of the energy used to transmit information from the sensor through the transmissive section. For example, the energy which interacts with the analyte can be in the infrared region of the light spectrum, whereas the energy used to transmit information can be in the visible region of the light spectrum.

The present invention also provides a sensor for detecting the presence of an analyte in an environment being tested. The sensor includes a housing, an energy source within the housing, at least one detector within the housing adapted to detect interaction between energy emitted by the energy source and the analyte, a transmissive section in the housing through which energy emitted from the energy source can be transmitted and a controller within the housing in operative connection with the energy source to modulate emission of energy from the energy source in a manner to communicate information through the transmissive section.

In one embodiment, the sensor is an infrared sensor and the energy source is an infrared energy source. The energy source, can emit energy over a range of wavelengths in the light spectrum. In this embodiment, the transmissive section can, for example, be a transmissive window. The housing can, for example, be an explosion-proof housing, particularly in the case of a sensor for combustible gases. Preferably, the sensor has at least a sensing mode in which the infrared energy source operates to interact with analyte that may be present in the test environment and a communication mode in which the controller modulates the energy source to communicate information through the window. The sensor preferably further includes at least one switch that can be activated in wireless manner from outside the housing to cause the sensor to enter the communication mode. As described above, activation of the switch can, for example, cause the sensor to enter a calibration mode.

The present invention also provides an infrared sensor system, including an infrared sensor as described above and a calibration cap adapted to be place in operative connection with the sensor housing. The calibration cap includes at least one activator adapted to affect the switch in a wireless manner to place the sensor in the calibration mode. The calibration cap can further include a communication detector sensitive to energy communicated through the window by the infrared energy source. The calibration cap can also include a display in communicative connection with the communication detector to display information transmitted via the infrared energy source.

In one embodiment, the sensor includes at least two switches at separate location within the housing, wherein both switches must be activated to place the sensor in a calibration mode. The calibration cap can, for example, include at least two magnets, wherein each of the magnets is placed in operative connection with one of the switches when the calibration cap is placed in operative connection with the sensor housing.

Other details, objects and advantages of the present invention will become apparent as the following description of the invention proceeds.

BRIEF DESCRIPTION OF THE DRAWINGS

In the accompanying drawings, preferred embodiments of the present invention and preferred methods of practicing the present invention are illustrated in which.

DETAILED DESCRIPTION OF THE INVENTION

In general, the devices, systems and methods of the present invention can be used to cause a sensor to enter a communication mode to communicate any type of information regarding the state, mode and/or operation of the sensor. In the representative embodiment discussed below, entry of an infrared sensor into a communication/calibration mode is described.

Figure 1A:
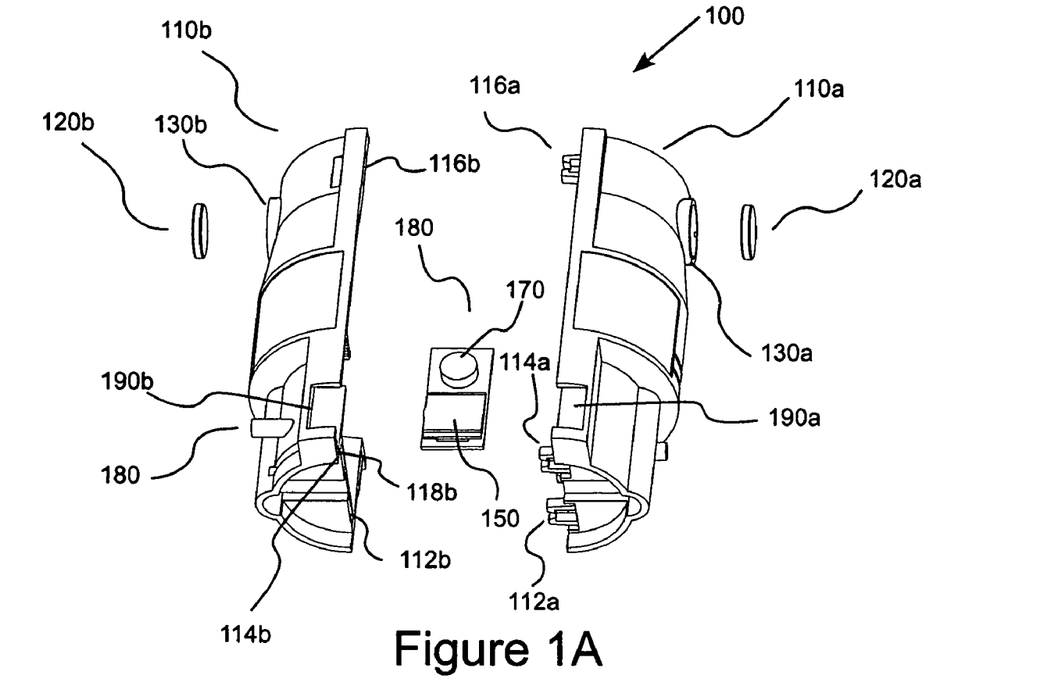
FIG. 1A illustrates a perspective view of one embodiment of a calibration cap of the present invention in an exploded or disassembled state.
Figure 1B:
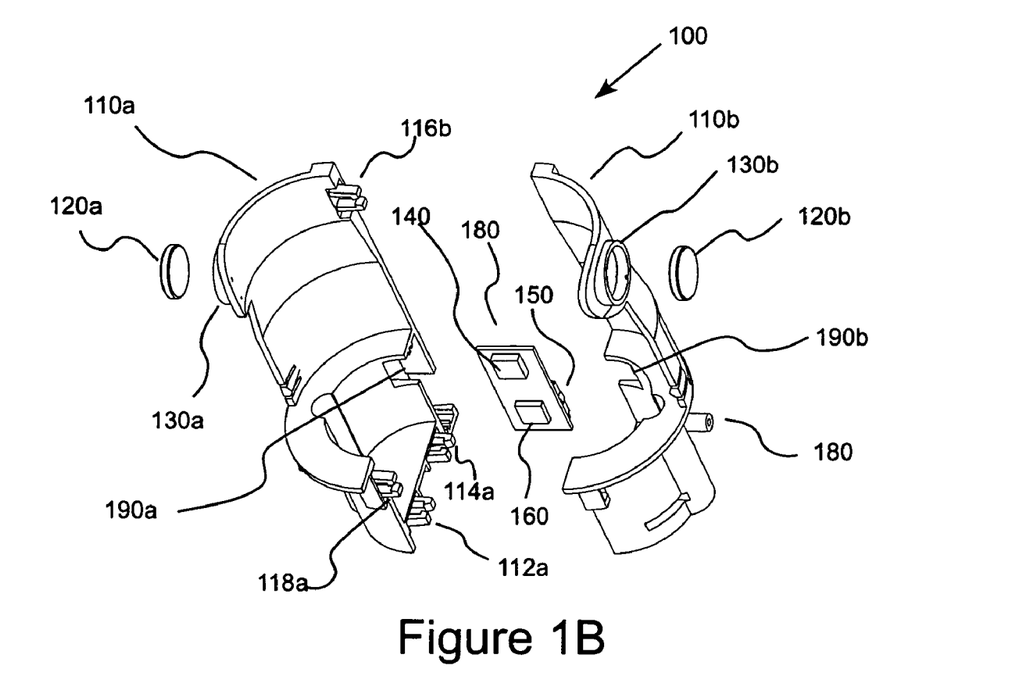
FIG. 1B illustrates another perspective view of the calibration cap of FIG. 1A in an exploded or disassembled state.
Figure 2A:
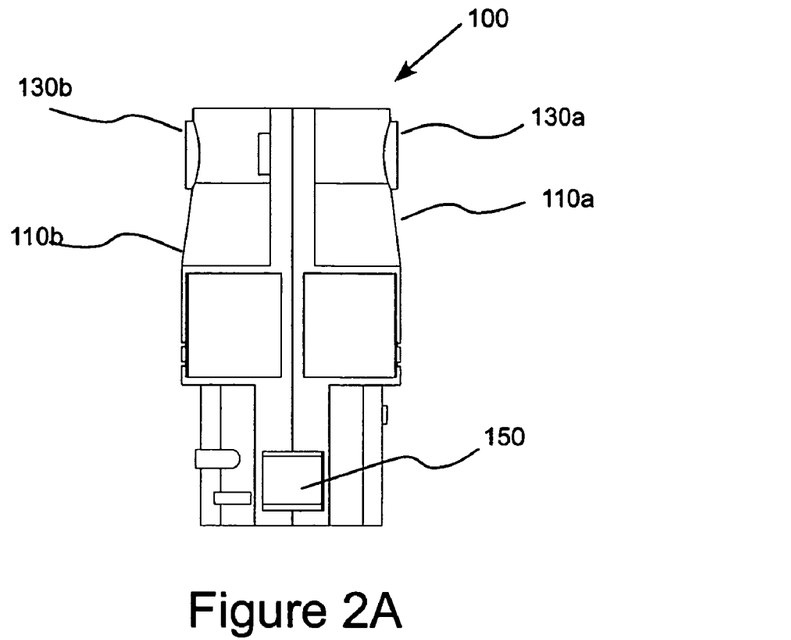
FIG. 2A illustrates a side view of the calibration cap of FIG. 1A in an assembled state.
Figure 2B:
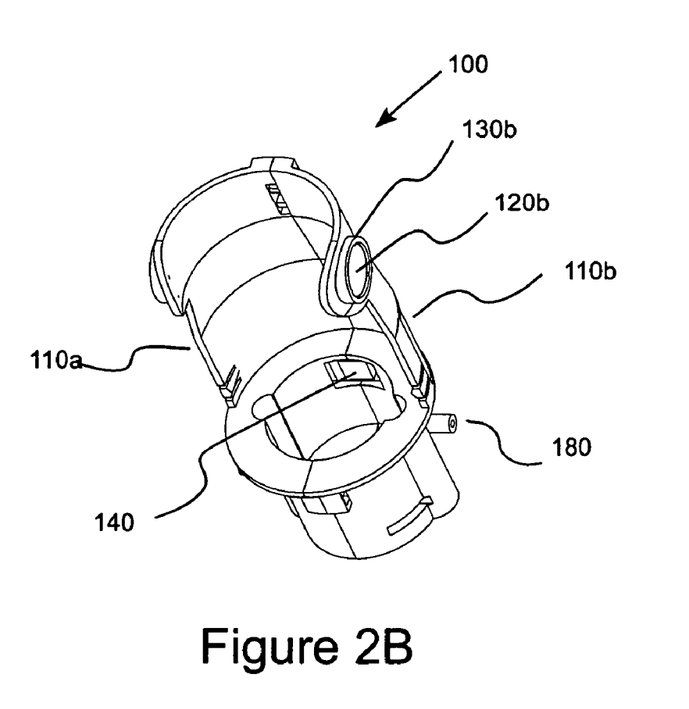
FIG. 2B illustrates a perspective view of the calibration cap of FIG. 1A in an assembled state.

In the embodiment of FIGS. 1A through 5 an infrared sensor calibration device, an infrared sensor calibration system and a method of calibrating an infrared sensor in which a calibration mechanism or calibrator 100 is placed in operative connection with a sensor 200 are illustrated. In this embodiment, calibration mechanism 100 can, for example, be formed as a cap or partial enclosure that is placed over or around sensor 200 so as to be in operative connection with sensor 200 as illustrated, for example, in FIGS. 4C and 4D. As illustrated in FIGS. 1A and 1B, in one embodiment, calibration cap 100 is formed as two connectible sections 110a and 110b which can, for example, be fabricated from a polymeric material such as polycarbonate. Connectors 112a, 114a, 116a and 118a of section 110a form a snap connection with corresponding receptors 112b, 114b, 116b and 118b in section 110b during assembly of calibrator 100. Calibrator 100 preferably includes at least one activator to communicate with sensor 200 to place sensor 200 in a calibration mode. In that regard, sensor 200 preferably has at least a first, sensing mode in which sensor 200 is operable to sense the concentration of the analyte in the test environment and a second, communication/calibration mode in which sensor 200 can be calibrated by, for example, application of a zero and/or a span gas, and in which sensor 200 is operable to communicate information regarding the calibration. If it is known that there is no analyte in the test environment, the test environment can be used as a zero gas during a zero calibration.

Preferably, the activator is operable to cause sensor 200 to enter the calibration mode in a wireless manner. Wireless activation of the calibration mode does not require that a port (to, for example, position a switch or a communication connection) be formed in housing 210 of sensor 100. Housing 210 for a combustible gas infrared sensor, for example, may be explosion proof, and it is often cumbersome and/or expensive to form ports in such housings while maintaining the explosion proof nature of the housing. In the embodiment of FIGS. 1A through 5, at least one magnet 120a is used as an activator to place sensor 200 in a calibration mode. In that regard, sensor 200 includes at least one activation element or switch 220a within housing 210 that is affected by the magnetic field of magnet 120a to change the mode or state of sensor 200 from the sensing mode to the calibration mode when calibrator cap 100 is in operative connection with sensor 200. Preferably, at least two magnets 120a and 120b are provided in calibrator 100 to cooperate with at least two corresponding switches 220a and 220b. Providing at least two sets of magnet/switch combinations positioned at different spatial locations greatly reduces the chance that a stray magnetic field could undesirably place sensor 200 in the calibration state or mode. In the embodiment of FIGS. 1A through 5, magnets 120a and 120b are positioned within seatings 130a and 130b, respectively, formed in sections 110a and 110b, respectively, of calibrator 100. When calibrator 100 is placed in operative connection with sensor 200, magnet 120a is placed in general alignment/operative connection with switch 220a, and magnet 120a is placed in general alignment/operative connection with switch 220b. Preferably, both of switches 220a and 220b must be activated by the corresponding magnets to place sensor 200 in the calibration mode. Additional activator/switch sets can be provided at distinct locations to, for example, instruct sensor 200 to enter into other communication modes or to communicate other information by activation of selected switches. As discussed above, however, preferably at least two switches must be activated to change the mode of the sensor 200 from a sensing mode to a communication mode.

Figure 3A:
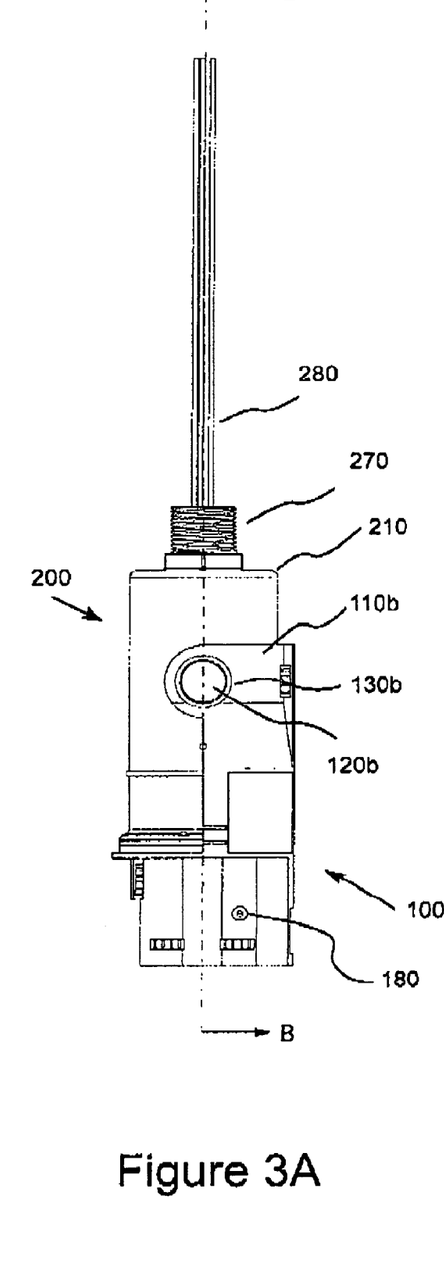
FIG. 3A illustrates a side view of the calibration cap of FIG. 1A in operative connection with an infrared sensor.
Figure 3B:
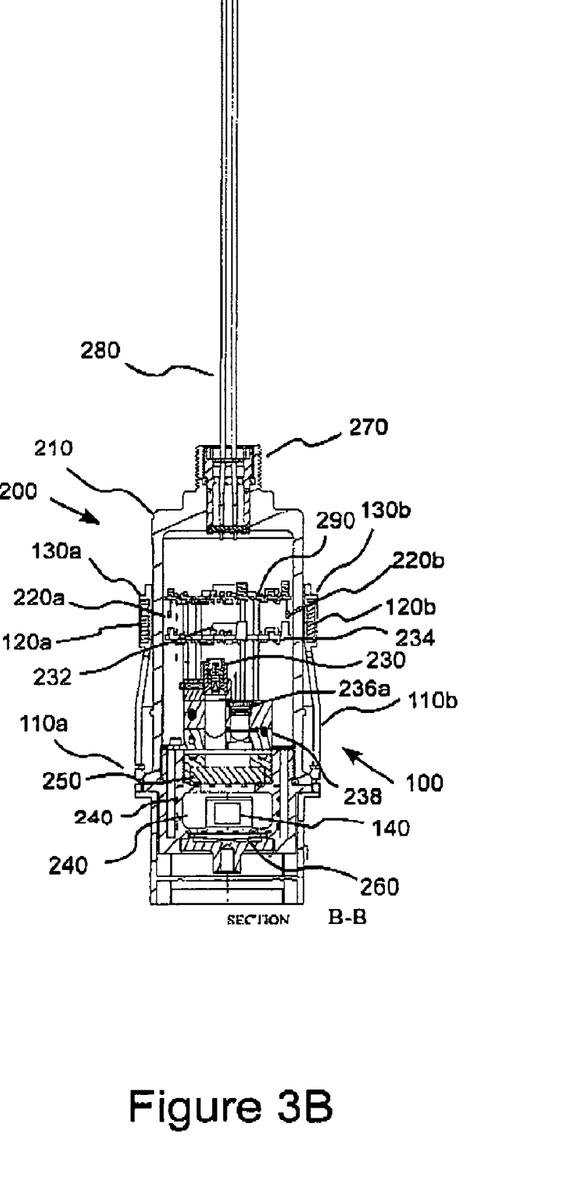
FIG. 3B illustrates a cross-sectional view of the calibration cap of FIG. 1A in operative connection with an infrared sensor.

The operation of sensor 200, in its sensing mode, is somewhat similar to the operation of the sensor of the ULTIMA XIR Gas Monitor available from Mine Safety Appliances Company. During the sensing mode, infrared energy source 230 is modulated at a specified frequency and directed into chamber 240. The modulation of infrared energy source 230 can, for example, be controlled via a microprocessor 232, which is positioned upon a printed circuit board 234 within sensor 200. The light passes through window 250 (for example, a sapphire window) into open volume 240 represented generally, for example, by dashed lines in FIG. 3B. The light is reflected by a generally concave mirror 260 to impinge upon detectors 236a and 236b (not shown in the cross-section of FIG. 3B as it is out of the plane of the cross-section) which are in optical connection with chamber or volume 240. In the embodiment of FIG. 3B, infrared energy source 230 and detectors 236a and 236b are securely seated in a seating block or optical block 238. Detectors 236a and 236b convert the infrared energy into electrical signals. Each of detectors 232a and 232b is sensitive to a different range of wavelengths in the infrared portion of the spectrum. As discussed above, the presence of an analyte gas in volume 240 reduces the intensity of the source emission measured by the analytical detector but not the intensity of the source emission measured by the reference detector. A microprocessor such as microprocessor 232 monitors the ratio of these two signals and correlates the ratio into a concentration reading.

As known in the art, sensor 200 can, for example, be positioned or connected in its operating position via a threaded connector 270. Power and communication wires 280 pass through a channel formed in threaded connector 270. A printed circuit board 290 is in operative connection with wires 280 and controls communication of sensor 200 with a control center (not shown) remote from sensor 200 in which a monitoring individual can view a display of sensor output and provide input signals to sensor 200. As described below, printed circuit board 290 also receives signals from calibration cap 100 to place sensor 200 in a calibration/communication mode. Unlike previous infrared gas monitoring systems, there is no need for a specialized monitoring unit equipped with a display to be directly connected to sensor 200.

Figures 4A, 4B:
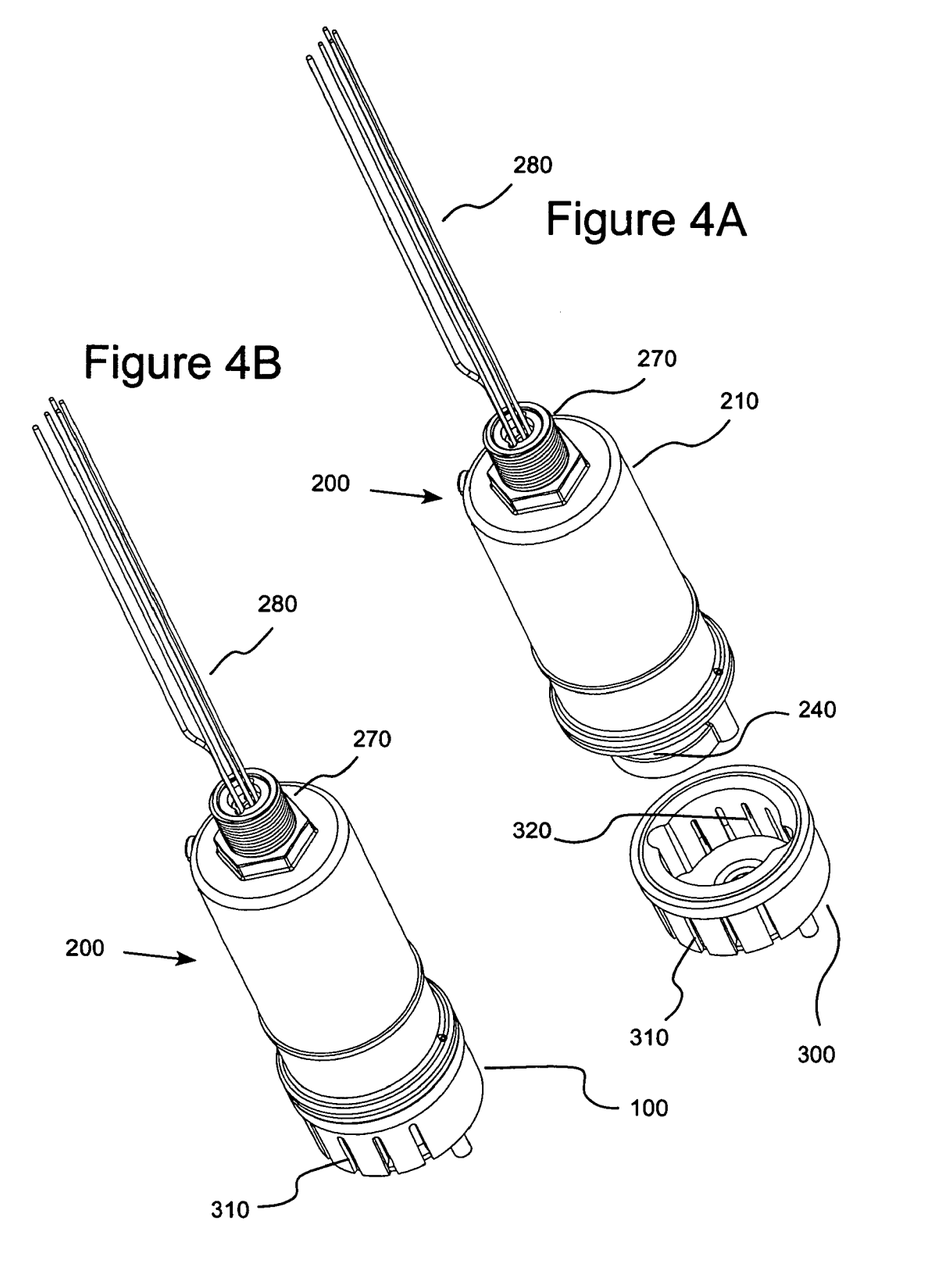
FIG. 4A illustrates a perspective view of a protective or environmental cap in alignment to be placed in operative connection with an infrared sensor.
FIG. 4B illustrates a perspective view of the environmental cap of FIG. 4A in operative connection with an infrared sensor.
Figures 4C, 4D:
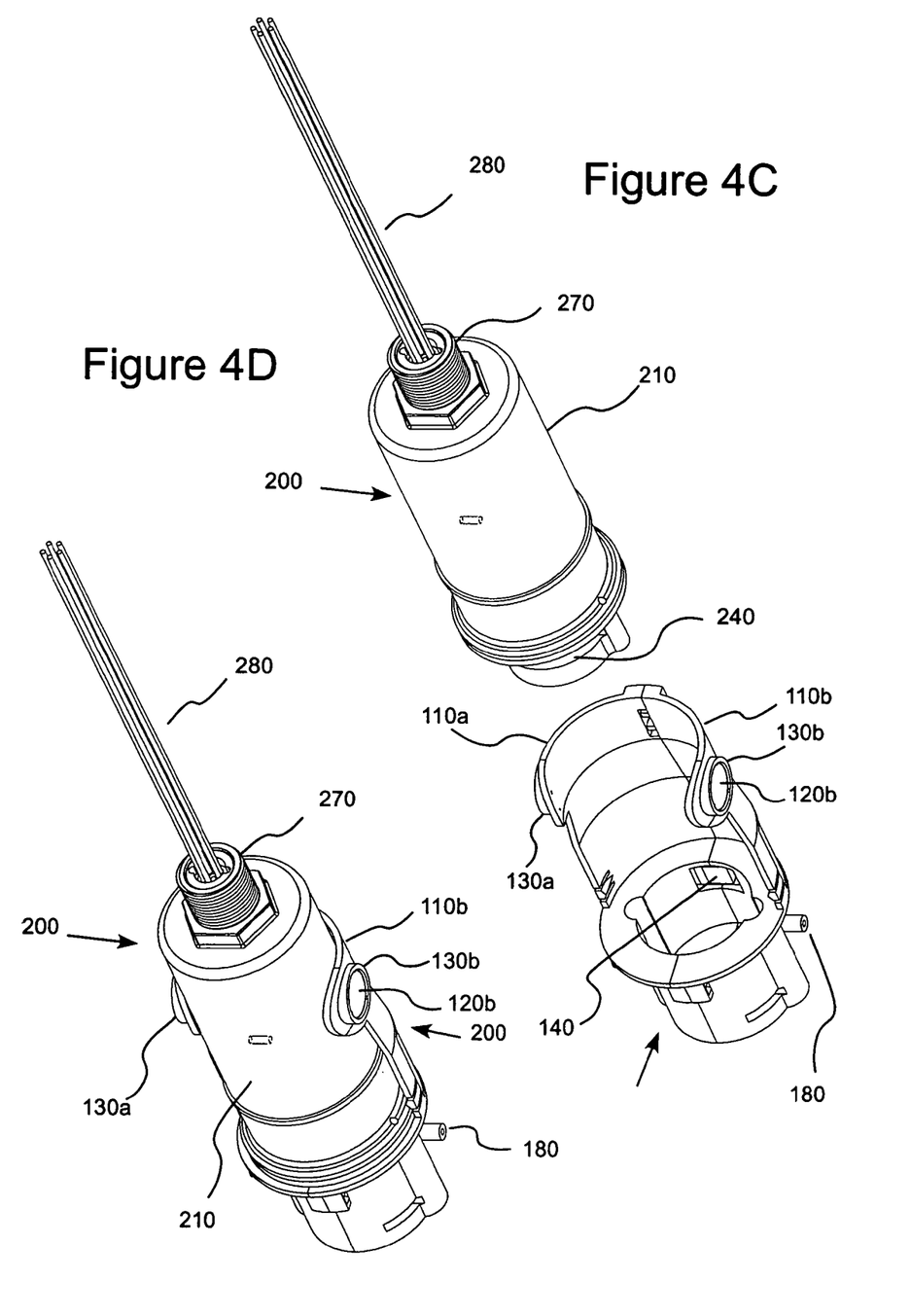
FIG. 4C illustrates a perspective view of the calibration cap of FIG. 1A in alignment to be placed in operative connection with an infrared sensor.
FIG. 4D illustrates a perspective view of the calibration cap of FIG. 1A in operative connection with an infrared sensor.

FIGS. 4A illustrates sensor 200 with a protective or environmental cap 300 positioned for attachment thereto, while 4B illustrates sensor 200 and environmental cap 300 in a connected state. Environmental cap 300 includes ports 310 through which gas from the surrounding environment can pass into volume 240 while sensor 200 is in the sensing mode. Ports 310 preferably do not provide a direct or straight path for diffusion of gas into volume 240 so that the pressure/force changes associated with wind are not transmitted through ports 310 into volume 240. For example, in the embodiment illustrated in FIG. 4A and 4B, external ports 310 are out of alignment with internal ports 320, with which external ports 310 are in fluid connection. Environmental cap 300 also preferably prevents other environmental elements such as snow and rain from passing into volume 240 while sensor 200 is in the sensing mode.

To enter the communication/calibration mode, environmental cap 300 is first removed from connection with sensor 200. Subsequently, calibration cap 100 is placed in operative connection with sensor 200, so that switches 220a and 220b, which are in operative connection with printed circuit board 290, are activated, thereby placing sensor 200 in the calibration mode. Activation of switches 220a and 220b can, for example, cause printed circuit board 290 to transmit a signal to microprocessor 232 on printed circuit board 234 to cause sensor 200 to enter into the calibration mode. Alternatively, activation of switches 220a and 220b can, for example, cause blockage or interruption of the energy emanating from infrared energy source 230 in a predotennined nianner (distinguishable from a failure of infrared energy source 230) such that the detectors of PCB 234 recognize entiy of the calibration mode. In the calibration mode3 infrared energy source 230 operates to calibrate sensor 200 as well as to communicate information regarding the calibration of sensor 200 through a tranamissive window 250 (see FIG. 3B).

To enter the communication/calibration mode, environmental cap 300 is first removed from connection with sensor 200. Subsequently, calibration cap 100 is placed in operative connection with sensor 200, so that switches 220a and 220b, which are in operative connection with printed circuit board 290, are activated, thereby placing sensor 200 in the calibration mode. Activation of switches 220a and 220b can, for example, cause printed circuit board 290 to transmit a signal to microprocessor 232 on printed circuit board 234 to cause sensor 200 to enter into the calibration mode. Alternatively, activation of switches 220a and 220b can, for example, cause blockage or interruption of the energy emanating from infrared energy source 230 in a predotennined nianner (distinguishable from a failure of infrared energy source 230) such that the detectors of PCB 234 recognize entey of the calibration mode. In the calibration mode3 infrared energy source 230 operates to calibrate sensor 200 as well as to communicate information regarding the calibration of sensor 200 through a tranamissive window 250 (see FIG. 3B).

Figure 5:
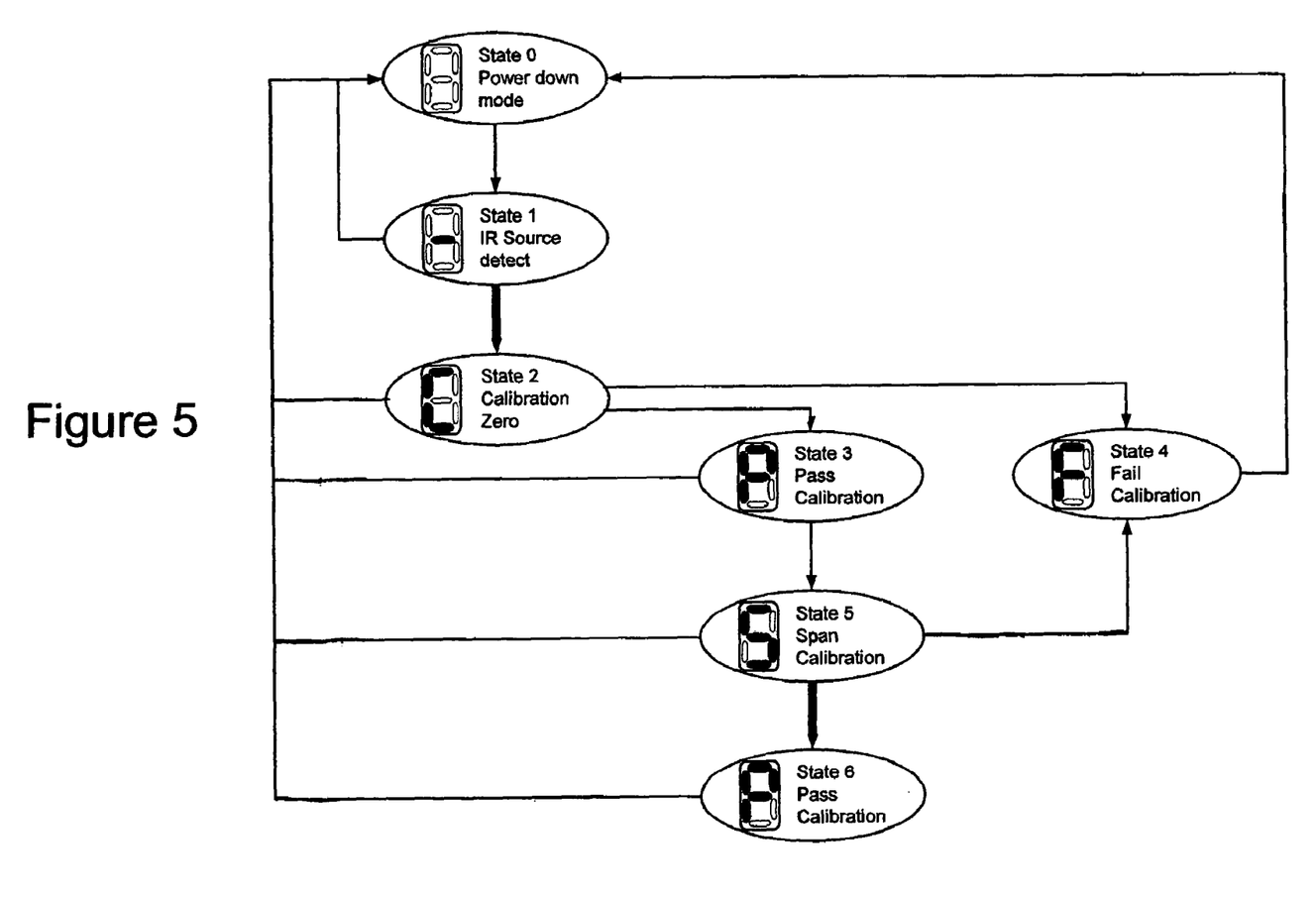
FIG. 5 illustrates an embodiment of a calibration protocol for a sensor of the present invention in the form of a flow chart.

Activation of the calibration mode can, for example, cause microprocessor 232 to first modulate infrared energy source 230 in a manner to communicate that the calibration mode has been recognized/activated. For example, light from infrared energy source 230 can be pulsed significantly faster or significantly slower than during the sensing mode to indicate entry of the calibration mode. Similarly, other information can be transmitted by. for example, varying the pulse/duration of infrared energy source 230. Infrared energy source 230 can also, for example, be modulated/pulsed to transmit information in a digital format. Infrared energy source 230 can emit light in the visible spectrum so that a user can directly visualize the signal through window 250. Alternatively, as illustrated in the embodiment of FIGS. IA through 5, calibrator cap 100 can include a detector 140 that is placed in operative connection with volume 240 as illustrated, for example, in FIG. 3B. Detector 140 is suitable to detect energy transmitted from infrared energy source 230 through window 260 and impinging upon detector 140. In the illustrated embodiment, detector 140 is in operative communication with a display 150 via a microprocessor 160. Power can, for example, be supplied to detector 140, display 150 and microprocessor 160 via a battery 170. Each of detector 140, display 150, microprocessor 160 and battery 170 can, for example, be positioned upon a printed circuit board 180. Printed circuit board 180 is seated in a seating formed by seating sections 190a and 190b of housing sections 110a and 110b, respectively.

In the case of use in environments in which combustible gases may be present, calibration cap 100, including printed circuit board 180 and all components thereot are preferably intrinsically safe as set forth in the UL913 Intrinsic Safety standard of underwriters Laboratories Inc. Although manufacturing calibration cap 100 to be intrinsically safe adds manufacturing costs, a single calibration cap 100 of the present invention can be used with any number of gas sensors 200. Moreover, the calibration system of the present invention climinatcs the need for explosion-proof monitoring units at the sensor location as well as explosion proof or intrinsically safe "intelligent"calibrators commonly used in connection with such monitoring units.

FIG. 5 illustrates a flow chart for one embodiment of a calibration protocol of the present invention. In this embodiment, once calibration cap 100 is placed in operative connection and detector 140 begins to detect the modulation of infrared energy source 230, which is being modulated at its sensing frequency (for example, 1 Hz), a dash is displayed on display 150. After a set period of time, the frequency of modulation of infrared energy source 230 is altered by controller/microprocessor 232 (to, for example, 2 Hz). This change in modulation is detected by detector 140 in combination with microprocessor 160, which causes a "C" to be displayed on display 150 to indicate to the individual calibrating sensor 200 that the individual should begin application of zero gas to the sensor (via, for example, gas port 180 formed in calibration cap 100) within a predetermined period of time (for example, 30 seconds). After this period of time, infrared energy source 230 is modulated at its sensing modulation until a steady state signal is reached. If sensor 200 passes the zero calibration, infrared energy source is modulated at a frequency such that a "P" is displayed upon display 150. At this point, the calibrating individual can remove the calibration cap 100 from sensor 200 to end the calibration and return sensor 200 to the sensing mode. While calibration cap 100 is in operative connection with sensor 200, a signal is preferably sent to the control center display (not shown) to let a person monitoring the control room display know that a calibration is in process. If the zero calibration fails, the frequency of modulation of infrared energy source is altered so that an "F" is displayed upon display 150. If the zero calibration fails, sensor 200 can be removed for service and/or replaced.

In the embodiment of FIG. 5, if calibration cap 100 remains in operative connection with sensor 200 for a sufficient period of time after a zero calibration is passed, infrared energy source 230 is modulated so that an "S" is displayed upon display 150. This display indicates to the individual calibrating sensor 200 that the individual should begin application of span gas to sensor 200 within a predetermined period of time (for example, 30 seconds). After this period of time, infrared energy source 230 is modulated at its sensing modulation until a generally steady state signal is reached. If sensor 200 passes the span calibration, infrared energy source is modulated at a frequency such that a "P" is displayed upon display 150. At this point, the calibrating individual can remove the calibration cap 100 from sensor 200 to end the calibration and return sensor 200 to the sensing mode. If the span calibration fails, the frequency of modulation of infrared energy source is altered so that an "F" is displayed upon display 150. As clear to one skilled in the art, may alternative communication/calibration protocols to the protocol set forth in FIG. 5 are possible.

The foregoing description and accompanying drawings set forth preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A method of communicating information from a sensor, the sensor including a source of energy within an explosion-proof housing thereof; energy from the energy source interacting with an analyte in a detectable manner, the sensor further having at least one transmissive section in the housing through which energy can be transmitted, the method comprising:

placing a calibration cap in operative connection with the sensor; communicating a wireless signal from the calibration cap to the sensor to place the sensor in a calibration mode;

modulating the emission of energy from the energy source in a manner that corresponds to information related to the calibration mode to be transmitted from the sensor through the transnissive section;

receiving the modulated emission of energy transmitted through the tranamissive section formed in the explosion-proof housing by a detector on the calibration cap; and displaying information corresponding to the modulated emission of energy on a display of the calibration cap.

2. The method of claim 1 wherein the sensor has at feast a sensing mode in which the energy source operates to interact with an analyte that may be present in an environment being tested and a communication mode in which the energy source operates to communicate information through the transmissive section.

3. The method of claim 2 wherein energy source is an infrared energy source and the transmissive section is a window in the housing of the sensor.

4. The method of claim 3 wherein the infrared energy source emits energy in the visible range of the spectrum in the communication mode.

5. The method of claim 3 wherein the step of placing the calibration cap in operative connection with the sensor places at least one magnet in operative connection with the calibration cap in operative connection with the housing to be in operative connection with a switch within the housing of the sensor.

6. The method of claim 3 wherein the step of placing the calibration cap in operative connection with the sensor places at least two magnets in operative connection with the calibration cap in operative connection with the housing at two distinct locations, each of the magnets being placed in operative connection with a separate switch within the housing of the sensor.

7. The method of claim 6 wherein the magnets are seated in the calibration cap.

8. The mothod of claim 7 wherein the infrared energy source is first modulated in a manner to detect the analyte during a calibration.

9. The method of claim 8, wherein the infrared energy source is subsequently modulated In a manner to indicate whether the calibration passed or failed.

10. The method of claim 9 wherein the calibration is a zero calibration.

11. The method of claim 1 wherein the energy source emits energy in the visible light spectrum to transmit information from the sensor through the tranamissive section.

12. A sensor for detecting the presence of an analyte in an environment being tested, the sensor comprising:

an explosion-proof housing;

an energy source within the housing; at least one detector within the housing adapted to detect interaction between energy emitted by the energy source and the analyte;

a transmissive section in to housing through which energy emitted from the energy source can be transmitted;

a controller within the housing in operative connection with the energy source to modulate emission of energy from the energy source in a manner to communicate information through the transmissive section; and at least a first switch within the housing, the sensor having at least a sensing mode in which the energy source operates to interact wit analyte that may be present in the test environment and a communication mode in which the controller modulates the energy source to communicate information through the window, the first switch being adapted to be activated from outside the housing by placing a magnet in operative connection with the housing to cause the sensor to enter the communication mode.

13. The sensor of claim 12 wherein the sensor is an infrared sensor and the energy source is an infrared energy source, the transmissive section being a window.

14. The sensor of claim 13 wherein the infrared energy source emits enemy in the visible range of the spectrum in the communication mode.

15. The sensor of claim 12 further comprising at least a second switch at a different position within the housing than the first switch and wherein at least two magnets must be placed in operative connection with the housing at two different locations to activate the first switch and the second switch to cause the sensor to enter the communication mode.

16. The sensor of claim 12 wherein activation of the first switch further causes the sensor to enter a calibration mode.

17. A infrared sensor system, comprising: an
infrared sensor, the sensor comprising:
a housing; an infrared energy source within the housing;
at least one detector within the housing adapted to detect interaction between energy emitted by the infrared energy source and the analyte;
a window in the housing through which energy emitted from the infrared energy source can be transmitted;
a controller within the housing in operative connection with the infrared energy source to modulate emission of energy from the infrared energy source; and
at least one switch operable to change a mode of the sensor from a sensing mode in which the infrared energy source operates to interact with analyte that may be present in the test environment to a calibration mode in which the controller modulates the energy source to communicate information regarding calibration of the sensor through the window; and
a calibration cap adapted to be placed in operative connection with the sensor housing, the calibration cap comprising at least one activator adapted to affect the switch in a wireless manner to place the sensor in the calibration mode, the calibration cap further comprising a communication detector sensitive to energy communicated through the window by the infrared energy source and a display in communicative connection with the communication detector to display information transmitted via the infrared energy source.

18. The infrared sensor system of claim 17 wherein the calibration cap further comprises at least one magnet adapted to operatively communicate wit the at least one switch of the sensor to change the mode of the sensor.

19. The infrared sensor system of claim 17 wherein the sensor comprises at least two switches at separate location within the housing, wherein both switches must be activated to place the sensor in a calibration mode, the calibration cap comprising at least two magnets, each of the magnets being placed in operative connection with one of the switches when the calibration cap is placed in operative connection with the sensor housing.

* * * * *